United States Patent [19]
Kraus et al.

[11] Patent Number: 5,902,281
[45] Date of Patent: May 11, 1999

[54] DRIP CHAMBER FOR INTRAVENOUS INFUSION

[75] Inventors: Menahem Kraus, Rehovot; Eli Shemesh, Ashdod; Haim Raz, Nes Ziona; Micha Ben-David, Sde Nehemia, all of Israel

[73] Assignee: Teva Medical Ltd., Ashdod, Israel

[21] Appl. No.: 08/894,506

[22] PCT Filed: Mar. 20, 1996

[86] PCT No.: PCT/US96/03985

§ 371 Date: Dec. 30, 1997

§ 102(e) Date: Dec. 30, 1997

[87] PCT Pub. No.: WO96/29104

PCT Pub. Date: Sep. 26, 1996

[30] Foreign Application Priority Data

| Mar. 22, 1995 | [IL] | Israel | 113090 |
| Jul. 5, 1995 | [IL] | Israel | 114467 |

[51] Int. Cl.⁶ .................................................. A61M 5/00
[52] U.S. Cl. .......................... 604/251; 604/80; 604/190; 604/252
[58] Field of Search ................... 604/80, 251, 151, 604/190, 252, 405, 406

[56] References Cited

U.S. PATENT DOCUMENTS

| 3,677,242 | 7/1972 | Shaye | 128/214 |
| 3,722,697 | 3/1973 | Burke et al. | 210/451 |
| 4,087,363 | 5/1978 | Rosemeyer et al. | 210/315 |
| 4,116,646 | 9/1978 | Edwards | 55/159 |
| 5,098,407 | 3/1992 | Okamura | 604/248 |

*Primary Examiner*—John D. Yasko
*Assistant Examiner*—N. Kent Gring
*Attorney, Agent, or Firm*—Ladas & Parry

[57] ABSTRACT

The present invention relates to a drip chamber for an intravenous infusion set. The invention also relates to a method of making drip chambers, and further, to an intravenous infusion set including a drip chamber. The invention is provided with a drip chamber comprising a housing defining a chamber to be located in a vertical position and including an inlet at the top and an outlet at the bottom; a first hydrophilic filter covering the outlet effective, when wet, to permit the flow therethrough of a liquid and to block the flow therethrough of air; and a second hydrophilic filter covering the inlet also effective, when wet, to permit the flow therethrough of a liquid and to block the flow therethrough of air.

19 Claims, 4 Drawing Sheets

DRIP CHAMBER FOR INTRAVENOUS INFUSION

The present invention relates to a drip chamber for an intravenous infusion set. The invention also relates to a method of making drip chambers, and further, to an intravenous infusion set including a drip chamber.

Intravenous infusion sets commonly include drip chambers to enable the flow rate of the infusion liquid to be visually observed. It is frequently desirable to filter the infusion liquid at the time it is adminstered to the patient. A hydrophilic filter may be used for this purpose, as described for example in U.S. Pat. Nos. 4,013,072 and 4,521,212, since such filters, when wetted with the liquid, pass liquid but block air.

An object of the present invention is to provide a novel drip chamber of the type including a hydrophilic filter. Another object of the invention is to provide an intravenous infusion set including a drip chamber and a bypass arrangement to facilitate priming the infusion set. A further object is to provide a method of making a drip chamber having a filter.

According to one aspect of the present invention, there is provided a drip chamber for an intravenous infusion set, comprising: a housing defining a chamber to be located in a vertical position and including an inlet at the top and an outlet at the bottom; a first hydrophilic filter covering the outlet effective, when wet, to permit the flow therethrough of a liquid and to block the flow therethrough of air; and a second hydrophilic filter covering the inlet also effective, when wet, to permit the flow therethrough of a liquid and to block the flow therethrough of air.

Such a drip chamber is particularly useful in an intravenous infusion set for home self-treatment, in order to make the set usable as easily as possible by the user. A drip chamber including hydrophilic filters at both its inlet and outlet enables the drip chamber to be pre-connected into an infusion set with the infusion bag, and to be pre-primed, so all the patient has to do is to connect the intravenous tube to the outlet end of the drip chamber and start the infusion.

Thus, during storage and handling of infusion sets including a drip chamber having a hydrophilic filter only at the outlet end, air in the drip chamber could escape into the infusion bag, and consequently the drip chamber could fill and become ineffective. However, by providing the drip chamber with a hydrophilic filter at both its inlet and outlet ends, the infusion set may be pre-primed before being stored, in which case the hydrophilic filters at the two ends of the drip chamber become wet and thereby prevent air from escaping either way, so that the drip chamber remains operational until used.

Such a construction, or one including a filter only at the outlet of the drip chamber, may also be used for fine filtration of the infusion liquid, e.g., for filtering out microorganisms. However, the flow rate through the filter would be quite low, and therefore it would generally be desirable to include an infusion pump to apply sufficient pressure for the desired flow rates. In order to permit priming of such an infusion set within a short time, the infusion set may be provided with a bypass for bypassing the drip chamber.

According to another aspect of the present invention, therefore, there is provided an intravenous infusion set comprising: a housing defining a chamber to be located in a vertical position and including an inlet at the top and an outlet at the bottom; a filter covering the outlet; bypass tubing connecting the inlet to the outlet and bypassing the chamber; and a valve in the bypass tubing, which valve is normally closed but is manually openable to bypass the chamber when priming the infusion set.

According to a further aspect of the present invention, there is provided a method of making a drip chamber, comprising: producing a cylindrical wall open at least at one end to constitute the bottom of the drip chamber; producing a bottom wall member including a circular wall integrally formed with a cylindrical skirt circumscribing the circular wall and formed with an annular seat around the cylindrical skirt at one side of the circular wall, and with a hollow stem extending axially from the center of the other side of the circular wall; securing a filter to the annular seat; and bonding the bottom wall member with the filter secured thereto to the open end of the cylindrical wall with the filter disposed within the cylindrical wall and the hollow stem projecting outwardly of the cylindrical wall.

According to a further preferred feature, the bottom wall member is bonded to the cylindrical wall by spin welding, i.e., by spinning one with respect to the other to produce frictional heat sufficient to weld the two together.

According to a further aspect of the present invention, there is provided a method of making a filtering type drip chamber, comprising: making a drip chamber including a cylindrical wall open at one end and closed at its opposite end by an end wall integrally formed with a hollow outlet stem; inserting through the open end a carrier member carrying a filter; moving the carrier member to the opposite end of the drip chamber to engage the end wall; and applying heat and pressure from the external side of the cylindrical wall to bond the carrier member to the cylindrical wall.

While the foregoing features are particularly useful for making drip chambers having hydrophilic filters at both its ends, it will be appreciated that the above-described method and bypass construction can also be used with respect to drip chambers having a single filter, e.g., at its outlet end.

Further features and advantages of the invention will be apparent from the description below.

The invention is herein described, by way of example only, with reference to the accompanying drawings, wherein.

Figure 2:
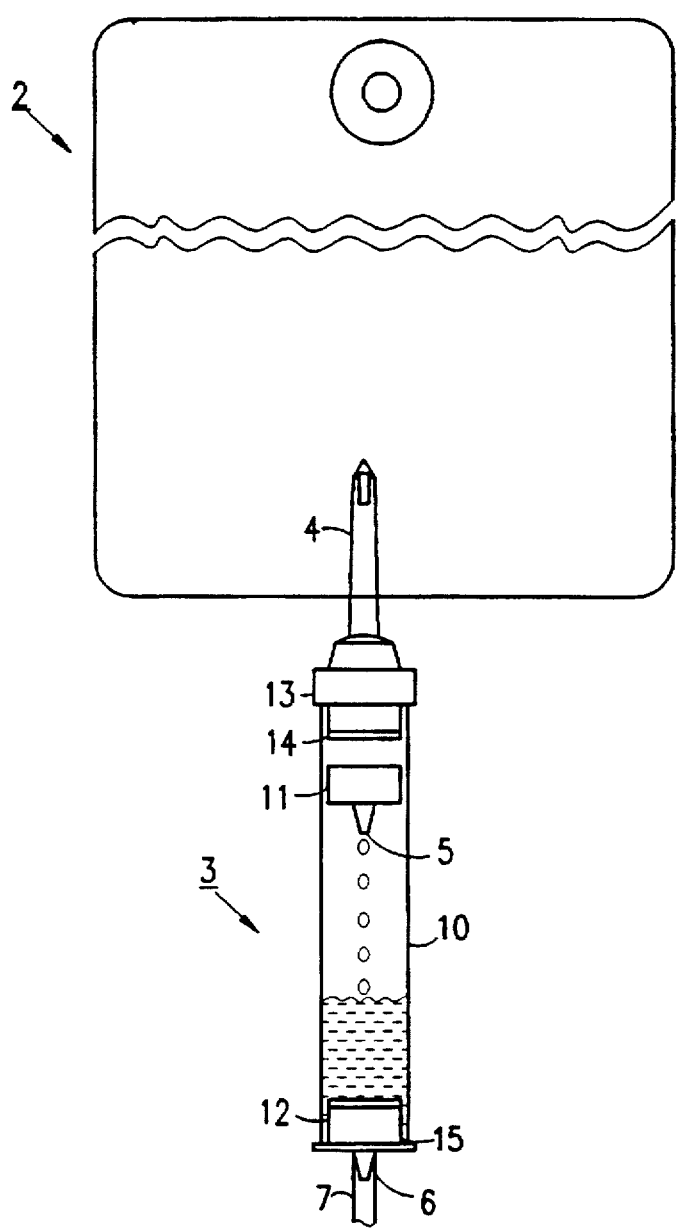
FIG. 2 illustrates the drip chamber of FIG. 1 in assembled form with an intravenous infusion set including an infusion bag.

FIG. 2 illustrates an intravenous infusion set for administering an infusion liquid, contained with an infusion bag 2, to a patient via a drip chamber 3 provided with a spike 4 for penetrating the infusion bag. At the time of administering the infusion liquid, the infusion bag 2 is suspended above the patient, and the drip chamber 3 is supported in a vertical position such that the flow rate of the infusion liquid may be observed by the rate of formation of drops of the infusion liquid from an inlet stem 5 into the drip chamber 3 during passage at the infusion liquid through outlet stem 6 and tube 7 leading to the patient.

Figure 1:
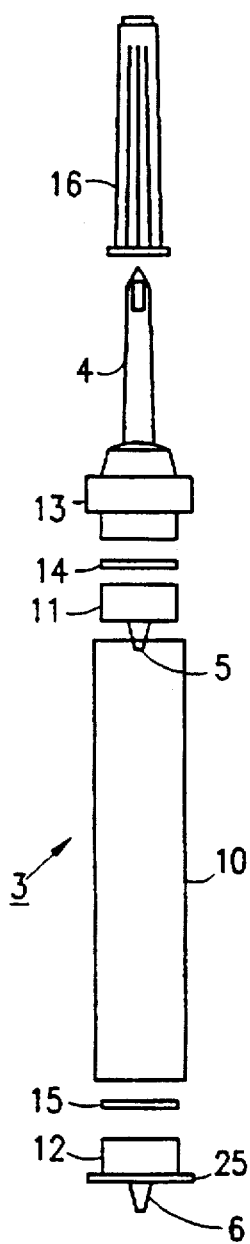
FIG. 1 is an exploded view illustrating the main components of one form of drip chamber constructed in accordance with the present invention.

FIG. 1 more particularly illustrates the construction of the drip chamber 3. It includes a cylindrical side wall 10 closed at its upper end by a top wall member 11 integrally formed with the inlet or drip stem 5, and closed at its bottom with a bottom wall member 12 integrally formed with the outlet stem 6. The inlet spike 4 is carried by an inlet fitting 13 applied over the top wall member 11. A hydrophilic filter membrane 14 is provided between the inlet fitting 13 and the top wall member 11. Another hydrophilic filter membrane 15 is provided over the bottom wall member 12.

The drip chamber assembly illustrated in FIG. 1 further includes a protector sleeve 16 which is normally applied over spike 4 during non-use or storage of the drip chamber. When the drip chamber is to be used, protector sleeve 16 is removed to enable the spike 4 to penetrate the infusion bag 2, as shown in FIG. 2.

It is desired to simplify as much as possible the use of the infusion set, e.g., for home self-treatment by the patient. For this purpose, the drip chamber 3 may be pre-connected to the infusion bag 2 and filled with the infusion liquid; and the set may then be pre-primed. Thus, all the patient would have to do is to suspend the infusion bag and the drip chamber over the patient (FIG. 2), connect the outlet tube 7 to the patient's intravenous cannula (not shown), and start the infusion.

Such an assembly could be stored for use with both hydrophilic filters 14 and 15 wetted by the infusion liquid. Hydrophilic filter 14 would thereby permit the infusion liquid to flow into the drip chamber via inlet stem 5, but would block the flow of air in either direction. Similarly, hydrophilic filter 15 would permit the infusion liquid to flow out of the drip chamber via outlet stem 6, but would also block the flow of air in either direction. Thus, air is prevented from escaping either way, and the drip chamber therefore remains essentially empty and operational until used.

Figure 3:
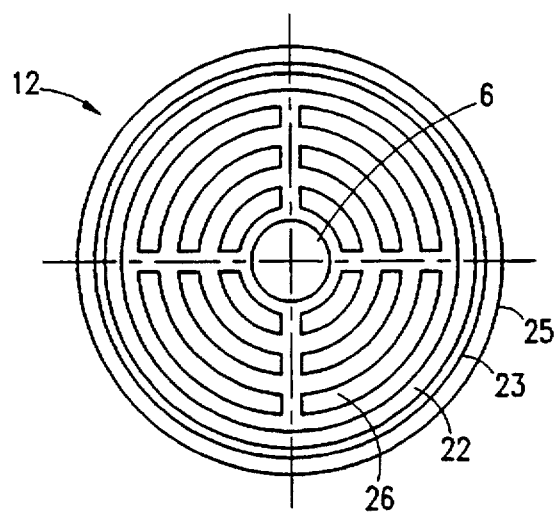
FIG. 3 is an enlarged plan view of the inner face of the bottom end wall of the drip chamber of FIG. 2 but without the hydrophilic filter.
Figure 4:
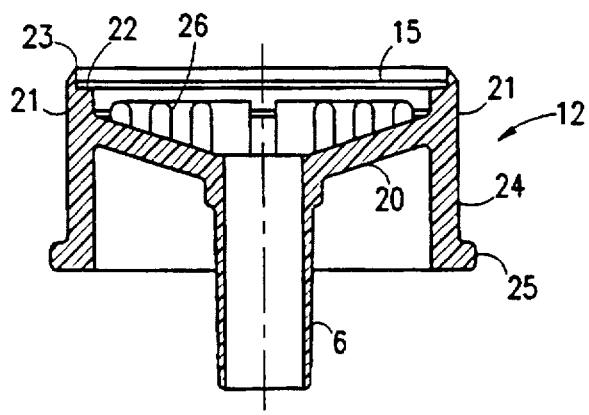
FIG. 4 is a sectional view of the bottom end wall of FIG. 3, including the hydrophilic filter to be mounted thereto before it is fixed to the bottom end wall.
Figure 5:
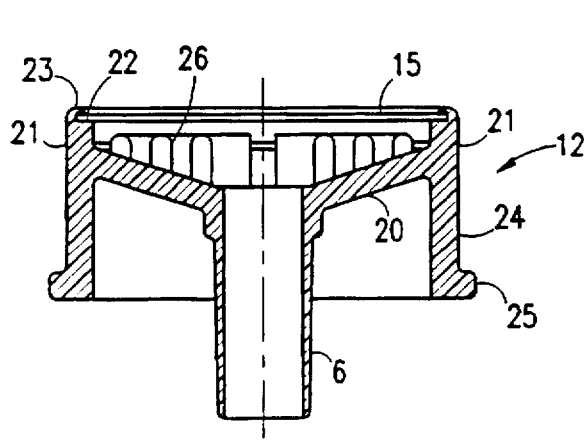
FIG. 5 is a view similar to that of FIG. 4 but after the hydrophilic filter has been fixed to the bottom end wall.

FIGS. 3–5 illustrate the construction of the bottom wall member 12, and particularly the manner of securing the hydrophilic filter 15 to it.

As shown particularly in FIGS. 4 and 5, the bottom wall member 12 includes a circular end wall 20 of conical configuration which closes the bottom of the drip chamber 3 except for the outlet stem 6, and an annular wall 21 around its circumference and formed with a flat annular seat 22 for receiving the hydrophilic filter 15. Annular seat 22 is circumscribed by an annular lip 23 rising above the upper surface of the hydrophilic filter membrane 15. The bottom wall member 12 is further formed with a cylindrical skirt 24 joining annular wall 21 and terminating in an outer annular rib 25 in its end opposite to that receiving the hydrophilic filter 15.

It will thus be seen that the outlet stem 6 is integrally formed on the outer surface of end wall 20, whereas the annular seat 22 receiving the hydrophilic filter 15 is formed on its inner surface so that the hydrophilic filter 15 will be disposed within the drip chamber 3 to overlie the outlet stem 6. The inner surface of end wall 20 is further formed with a plurality of circumferentially-extending spacer ribs 26 to space the hydrophilic filter 15 from the open end of the outlet stem 6.

Figure 6:
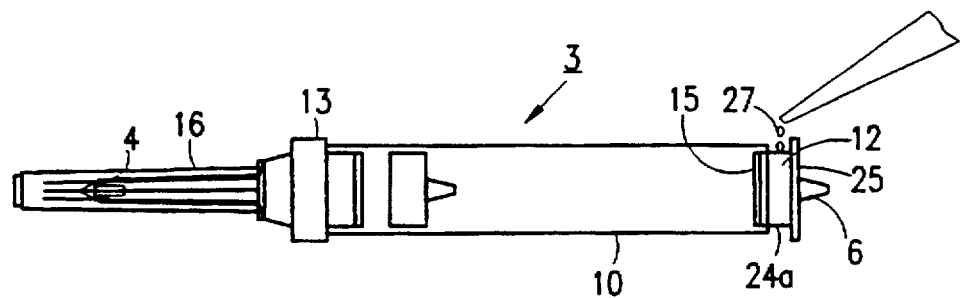
FIG. 6 illustrates one manner for fixing the bottom end wall, including the hydrophilic filter attached thereto, to the cylindrical side wall of the drip chamber.

The hydrophilic filter 15 may be sensitive to the solvent commonly used in adhesives. FIGS. 4–6 illustrate a manner of securing hydrophilic filter 15 to the the bottom wall member 12, and of securing the bottom wall member 12, together with the hydrophilic filter 15, to the bottom end of the cylindrical side wall 10 of drip chamber 3, such as to substantially protect the hydrophilic filter from exposure to the solvent of the adhesive.

After the hydrophilic filter 15 has been applied to the flat annular seat 22 of the bottom wall member 12 (FIG. 4), a heated swaging die (not shown) is applied to the annular lip 23 to turn the lip over onto the outer circumference of the hydrophilic filter 15 (FIG. 5), and thereby to secure the hydrophilic filter firmly to the bottom wall member 12. The bottom wall 12, including the hydrophilic filter 15 secured to it, is then secured to the bottom end of the cylindrical side wall 10 by inserting a portion of the cylindrical skirt 24 into the respective end of side wall 10, leaving a portion of skirt 24 outside as shown at 24a in FIG. 6. An adhesive 27 is applied to skirt portion 24a, and then the bottom wall 12 is completely inserted until its annular rib 25 abuts against the end of the side wall 10. This procedure bonds the bottom wall member 12 to the side wall 10 in a manner which substantially protects the hydrophilic filter 15 from exposure to the solvent of the adhesive.

Another preferred manner of bonding the bottom wall member 12 to the open end of the cylindrical wall 10 would be by spin welding. Thus, after the filter 15 has been secured to the annular seat 22 of the bottom wall member 12 in the manner described above, the bottom wall member is introduced through the open end of the cylindrical wall 10 with the filter disposed within the cylindrical wall, and the hollow stem projecting outwardly of the cylindrical wall. Then, either the bottom wall member 12 or the cylindrical wall 10 is rotated with respect to the other to produce sufficient friction to weld the bottom wall to the cylindrical wall.

The hydrophilic filter 14 at the inlet end of the drip chamber 3 may be secured in the same manner as described above. In this case, however, the hydrophilic filter 14 is secured to one end of the inlet fitting 13, rather than to the top wall member 11.

Figure 7:
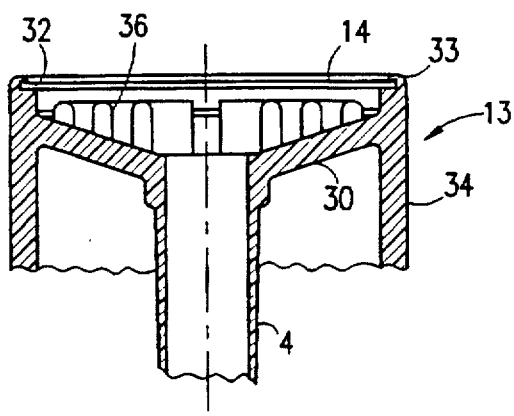
FIG. 7 illustrates one manner for fixing the hydrophilic filter at the inlet end of the drip chamber.

Thus, as shown in FIG. 7, the inlet fitting 13 is also formed with a circular end wall 30 adapted to be inserted into the inlet end of the drip chamber cylindrical side wall 10 after the top wall member 11 has been inserted and secured thereto. Before inlet fitting 13 is inserted into the cylindrical side wall 10, the hydrophilic filter 14 is applied to the flat inner seat 32 formed in the respective end of the inlet fitting, and is secured thereto by turning-over a lip 33, in the same manner as described above with respect to FIGS. 4 and 5 for fixing hydrophilic filter 15 on the flat annular seat 22. The inlet fitting 13 is also formed, on the opposite side of end wall 30, with a cylindrical skirt 34 which is received within the inlet end of the cylindrical side wall 10 of the drip chamber, and bonded to it in the same manner as the hydrophilic filter 15 is secured to the bottom end of the drip chamber, as described above with respect to FIG. 6.

Another manner of securing the hydrophilic filter 14 to the inlet end of the drip chamber would be to secure this filter to the top wall member 11, in the same manner as described above with respect to FIGS. 4 and 5. The top wall member 11 may then be secured to the upper end of side wall 10 by applying the adhesive to the inner surface of side wall 10 (e.g., by dipping or spraying), and then inserting the top wall member 11 together with the hydrophilic filter membrane 14. In such a case, the top wall member 11 may be constructed as the bottom wall member 12, except for the annular rib 25.

Figure 8:
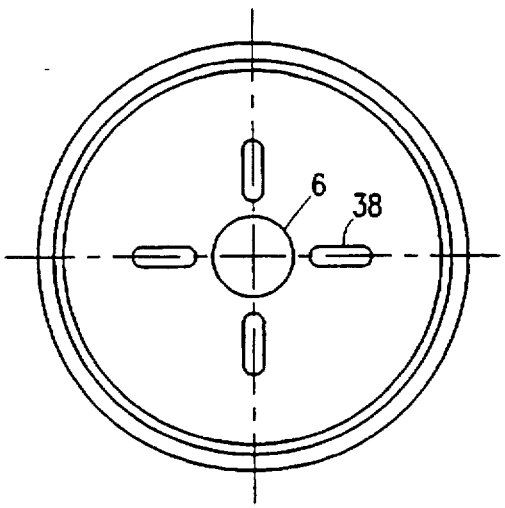
FIGS. 8 and 9 are plan views, corresponding to that of FIG. 3, illustrating other spacing rib configurations that may be used for spacing either or both hydrophilic filters from their respective end walls.
Figure 9:
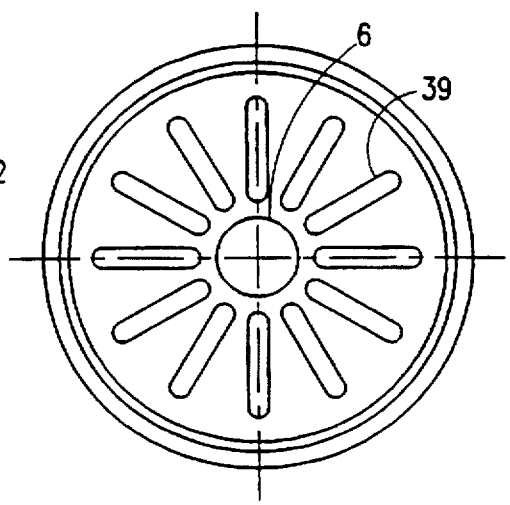

FIGS. 8 and 9 illustrate other constructions that may be used for the bottom wall member 12, as well as for the respective end of the inlet fitting 13, and for the top wall member 14. The constructions illustrated in FIGS. 8 and 9 are basically the same as described above, except that the spacing ribs, shown at 26 in FIGS. 3–5, are in the form of radially-extending ribs, as shown at 38 in FIG. 8, and at 39 in FIG. 9, respectively, radiating around the outlet stem 6.

Figure 10:
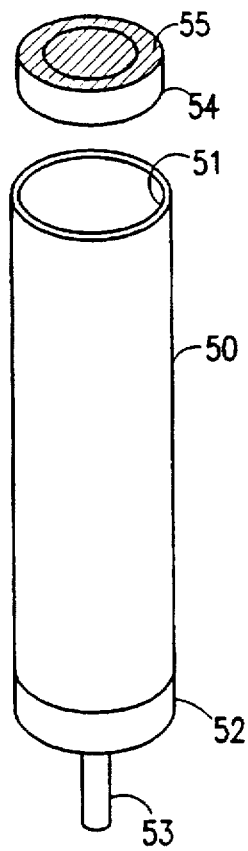
FIGS. 10, 11 and 12 illustrate another method that may be used for making a drip chamber having a filter.
Figure 11:
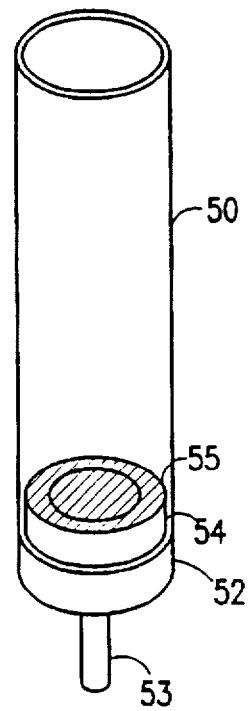
Figure 12:
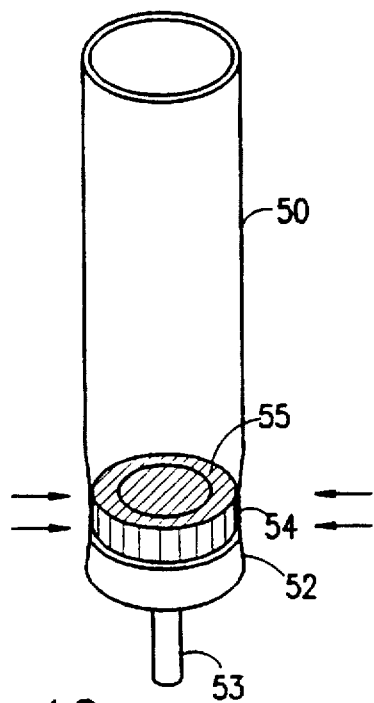

FIGS. 10–12 illustrate a still further method that may be used for making a drip chamber provided with a filter. In this method, a drip chamber of conventional construction is first produced to include a cylindrical wall 50 open at one end 51, and closed at its opposite end by an end wall 52 integrally formed with a hollow outlet stem 53. A carrier member 54 carrying a filter 55, e.g., a hydrophilic filter membrane, is inserted through the open end 51 of the cylindrical wall 50 and is moved therethrough to engage the end wall 52, as shown in FIG. 11. Heat and pressure are then applied from the external side of the cylindrical wall 50 to bond the carrier member to the cylindrical wall, as shown in FIG. 12.

Figure 13:
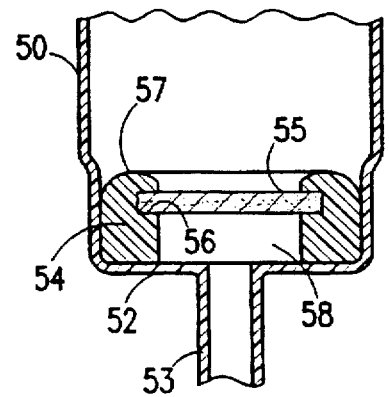
FIG. 13 is a fragmentary sectional view illustrating one example of the construction of a drip chamber made according to the method of FIGS. 10–12.

The construction of carrier member 54, including the manner in which the filter 55 is carried by it, is more particularly illustrated in FIG. 13. Thus, carrier member 54 is in the configuration of a cylindrical skirt formed at one end with a flat annular seat 56 for receiving the filter 55. The cylindrical skirt 54 is further formed with an annular lip 57 circumscribing seat 56. After filter 55 has been placed on seat 56, the annular lip 57 is turned over to engage the outer periphery of the filter 55 and thereby to firmly secure the filter to the outer periphery of the carrier member.

As also seen in FIG. 13, when carrier member 54 is moved to engage end wall 52 of the drip chamber, filter 55 is spaced from that end wall by a space 58.

Carrier member 54 may be a simple cylinder, without lip 57, with membrane 55 sealed to one of the flat surfaces by heat and pressure or other conventional sealing methods. Alternatively, the membrane may be molded into the carrier member.

A drip chamber including a filter at both its inlet and its outlet, or only at its outlet, may also be used for fine filtration of the infusion liquid. For example, an 0.2 μm rated membrane-type filter may be used for filtering out most common microorganisms. However, an infusion set including such a drip chamber would have a very low flow rate if gravity-fed.

Figure 14:
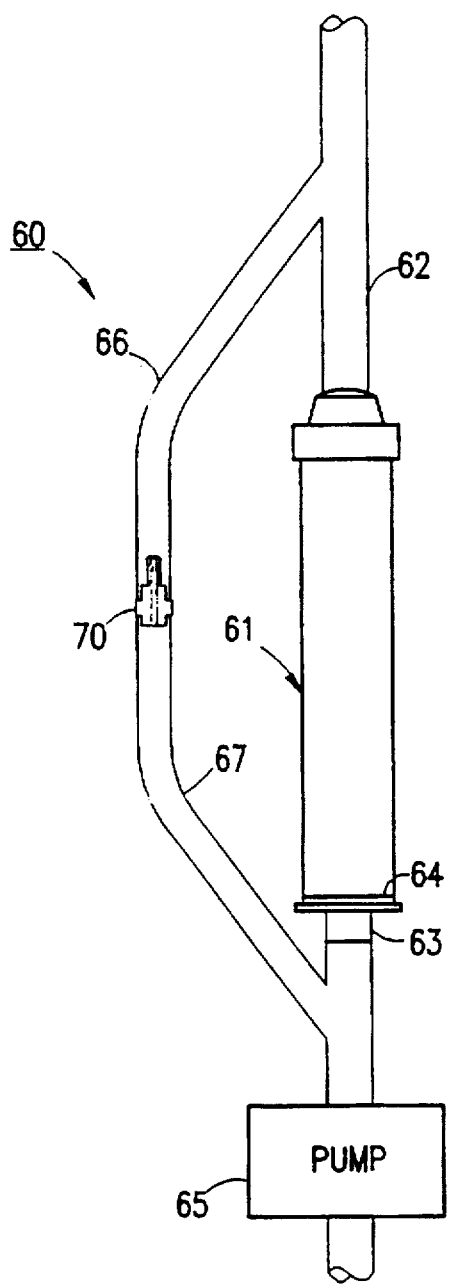
FIG. 14 illustrates an infusion set including a drip chamber, infusion pump, and a bypass tubing to facilitate priming the infusion set.

FIG. 14 illustrates an infusion set which includes an infusion pump for this purpose, and a special priming procedure to rid the infusion set of air before use. Thus, the infusion set 60 illustrated in FIG. 14 includes a drip chamber 61 having an inlet 62 at its upper end, an outlet 63 at its lower end, and a membrane-type filter 64 covering the outlet 63. Filter 64 may be of the hydrophilic type as described above to block air from entering the set downstream of the drip chamber, or it may be a fine filter, such as an 0.2 μm rated membrane, for filtering out microorganisms. The infusion set illustrated in FIG. 14 further includes an infusion pump 65 for applying sufficient pressure to the liquid downstream of the drip chamber 61 for the desired flow rates.

Figure 15:
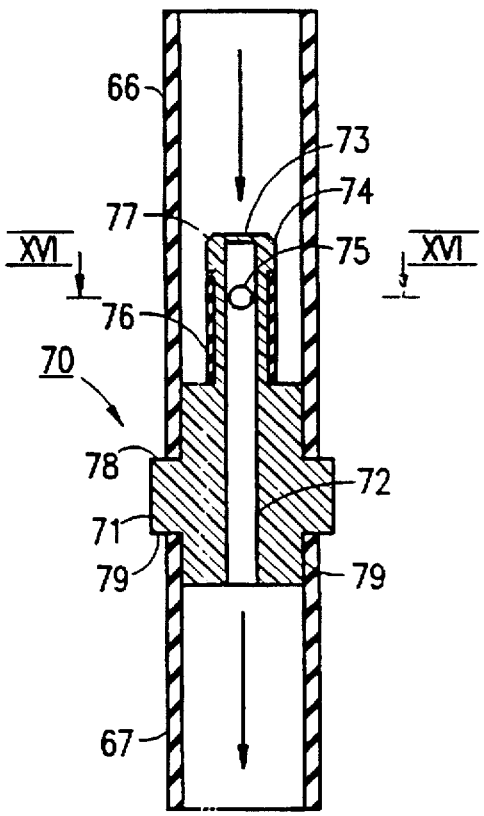
FIG. 15 is an enlarged, longitudinal-sectional view of the manually-openable valve in the bypass tubing of FIG. 14.
Figure 16:
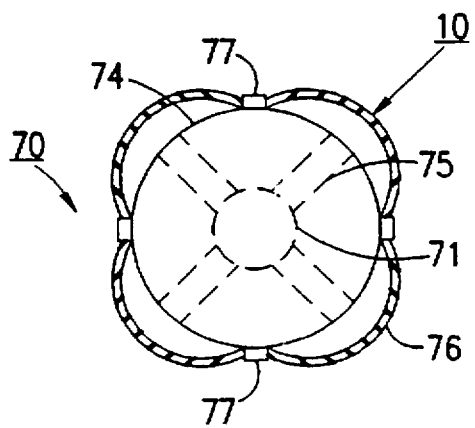
FIG. 16 is an enlarged sectional view along line XVI—XVI of FIG. 15.

In order to faciliate priming the infusion set, it includes bypass tubing 66, 67 connecting the inlet 62 to the outlet 63 for bypassing the drip chamber 61. The bypass includes a valve 70 which is normally closed but which is manually openable to bypass chamber 61 when priming the infusion set. A preferred construction for valve 70 is illustrated in FIG. 15 and 16.

Thus, valve 70 includes a cannula 71 having an axial passageway 72 from one of the cannula but closed at the opposite end by an end wall 73. The closed end 74 of cannula 71 is of smaller diameter than the open end of the cannula and is formed with a plurality of radial bores 75 adjacent the end wall 73 and leading from the axial passage 72 to the outer surface of the cannula. An elastomeric sleeve 76 overlies and normally closes the radial bores 75. A plurality of outwardly-projecting ribs 77 at the end wall 73 retain elastomeric sleeve 76 in place over the bores 75.

Cannula 71 is further formed with an annular seat 78 for receiving tube 66 leading to the inlet 62 of drip chamber 61, and with another seat 79 at the opposite side, receiving tube 67 leading to the outlet 63 of the drip chamber.

It will be seen that elastomeric sleeve 76 normally closes radial bores 75, so that valve 70 normally blocks the flow of liquid through the bypass 60 from the inlet 62 to the outlet 63 of the drip chamber 61. However, when it is desired to prime the infusion set, the user squeezes the elastomeric sleeve 76 at diametrically-opposed points, as shown in FIG. 16, between the radial bores 75. This causes the elastomeric sleeve to bulge outwardly at the locations of the radial bores, permitting the liquid to flow through the valve and therby bypass the drip chamber 61.

We claim:

1. A drip chamber for an intravenous infusion set, comprising: a housing defining a chamber to be located in a vertical position and including an inlet at the top and an outlet at the bottom; a first hydrophilic filter covering said outlet effective, when wet, to permit the flow therethrough of a liquid and to block the flow therethrough of air; and a second hydrophilic filter covering said inlet also effective, when wet, to permit the flow therethrough of a liquid and to block the flow therethrough of air.

2. The drip chamber according to claim 1, wherein said outlet includes an outlet stem integrally formed in the outer face of a bottom wall of the housing; said bottom wall having an inner face formed with a flat annular seat receiving said first hydrophilic filter, and with an annular lip around said annular seat; said annular lip being turned inwardly over the first hydrophilic filter to securely fix the first hydrophilic filter on said seat.

3. The drip chamber according to claim 2, wherein the inner face of said bottom wall is further formed with a plurality of spacing ribs for spacing the first hydrophilic filter from said bottom wall.

4. The drip chamber according to claim 1, wherein said inlet includes an inlet fitting carrying said second hydrophilic filter at one end, and a coupling member at the opposite end for coupling the fitting to an infusion liquid container.

5. The drip chamber according to claim 4, wherein said one end of the inlet fitting is formed with a flat annular seat receiving said second hydrophilic filter, and with an annular lip around said annular seat, said annular lip being turned inwardly over the second hydrophilic filter to securely fix the second hydrophilic filter on said seat.

6. The drip chamber according to either of claim 4, wherein said coupling member and at opposite end of the inlet fitting is a spike for penetrating an infusion bag.

7. The drip chamber according to claim 1, wherein said inlet includes an inlet stem integrally formed in a top wall of the housing and extending inwardly of the housing.

8. An intravenous infusion set including a drip chamber according to claim 1, in combination with a container for an infusion liquid connected to said inlet of the drip chamber.

9. An intravenous infusion set, comprising: a housing defining a drip chamber to be located in a vertical position and including an inlet at the top and an outlet at the bottom; a filter covering said outlet; bypass tubing connecting said inlet to said outlet and bypassing said drip chamber; and a valve in said bypass tubing, which valve is normally closed but is manually openable to bypass said drip chamber when priming the infusion set.

10. The infusion set according to claim 9, further including a pump for applying pressure to the liquid in said infusion set.

11. The infusion set according to either of claim 9, wherein said filter is a hydrophilic filter effective, when wet, to permit the flow therethrough of a liquid and to block the flow therethrough of air.

12. The infusion set according to claim 9, wherein said outlet includes an outlet stem integrally formed in the outer face of a bottom wall of the housing; said bottom wall having an inner face formed with a flat annular seat receiving said filter, with an annular lip around said annular seat and turned inwardly over the filter to securely fix it on said seat, and a plurality of spacing ribs for spacing the filter from said bottom wall.

13. A drip chamber for an intravenous infusion set, comprising: a cylindrical housing defining a chamber to be located in a vertical position and including a top wall having an inlet and a bottom wall having an outlet; a hydrophilic filter covering said outlet effective, when wet, to permit the flow therethrough of a liquid and to block the flow therethrough of air; said bottom wall including an outlet stem integrally formed in its outer face; said bottom wall having an inner face formed with a flat annular seat receiving said hydrophilic filter, and with an annular lip around said annular seat, said annular lip being turned inwardly over the hydrophilic filter to securely fix the hydrophilic filter on said seat wherein the inner face of said bottom wall is further formed with a plurality of spacing ribs for spacing the hydrophilic filter from said bottom wall.

14. The drip chamber according to either of claim 13, wherein said bottom wall is of circular configuration and is formed with a cylindrical skirt bonded to the cylindrical housing.

15. A method of making a drip chamber, comprising:

producing a cylindrical wall open at least at one end to constitute the bottom of the drip chamber;

producing a bottom wall member including a circular wall integrally formed with a cylindrical skirt circumscribing the circular wall and formed with an annular seat around the cylindrical skirt at one side of the circular wall, and with a hollow stem extending axially from the center of the other side of the circular wall;

securing a filter to said annular seat;

and bonding said bottom wall member with the filter secured thereto to said open end of said cylindrical wall with the filter disposed within the cylindrical wall and the hollow stem projecting outwardly of the cylindrical wall.

16. The method according to claim 15, wherein said bottom wall member is secured to said cylindrical wall by spin welding.

17. The method according to claim 15, wherein said filter is attached to said annular seat by forming said annular seat with an outer annular lip, placing the filter on said annular lip, and turning over said annular lip to attach said filter to said annular seat.

18. A method of making a filtering type drip chamber, comprising:

providing a drip chamber including a cylindrical wall open at one end and closed at its opposite end by an end wall integrally formed with a hollow outlet stem;

inserting through said open end a carrier member carrying a filter;

moving said carrier member to said opposite end of the drip chamber to engage said end wall;

and applying heat and pressure from the external side of the cylindrical wall to bond said carrier member to said cylindrical wall.

19. The method according to claim 18, wherein said carrier member is formed with a cylindrical skirt having one end mounting said filter, and its opposite end engageable with said end wall of the drip chamber at the time the heat and pressure are applied, to thereby space the filter from said end wall.

* * * * *